United States Patent [19]

Brushwyler et al.

[11] 4,036,722

[45] July 19, 1977

[54] FLOW THROUGH CELL ASSEMBLY

[75] Inventors: Gordon R. Brushwyler, Anaheim; Timothy F. Scott, Brea, both of Calif.

[73] Assignee: Robertshaw Controls Company, Richmond, Va.

[21] Appl. No.: 606,443

[22] Filed: Aug. 21, 1975

[51] Int. Cl.$^2$ .......................................... G01N 27/46
[52] U.S. Cl. ............................ 204/195 B; 204/195 R; 204/195 P
[58] Field of Search ............ 204/195 P, 195 B, 195 R, 204/195 M, 195 F, 195 G, 195 T, 195 S, 1; 324/29, 30 R, 30 B; 23/253 R

[56] References Cited

U.S. PATENT DOCUMENTS

| 3,151,052 | 9/1964 | Arthur et al. | 204/195 F |
| 3,234,562 | 2/1966 | Bell et al. | 204/1 T |
| 3,658,478 | 4/1972 | Spergel et al. | 23/253 R |
| 3,718,568 | 2/1973 | Neuwelt | 204/195 P |
| 3,813,325 | 5/1974 | Merrell et al. | 204/195 B |

Primary Examiner—G. L. Kaplan
Attorney, Agent, or Firm—Fulwider, Patton, Rieber, Lee & Utecht

[57] ABSTRACT

There is disclosed a flow through cell assembly that is particularly useful for housing of the sensing cathode of a dissolved oxygen cell. The flow through cell assembly supports the cathode of the dissolved oxygen cell adjacent the upper surface of a through passageway receiving flow of the liquid under investigation and includes a transversely positioned second probe that substantially blocks flow through the through passageway and provides an orifice area of restricted dimensions immediately beneath the dissolved substantially coplanar with the upper surface of the through passageway to avoid the formation of any air or gas pockets in the flow passageway which could cause erroneous indications on the dissolved oxygen probe. This also allows a high flow velocity across the sensor tip which permits lower volumetric flow rates and a proportionally greater sensitivity of continuous respirometer instrument utilizing the flow through cell assemblies.

4 Claims, 6 Drawing Figures

U.S. Patent  July 19, 1977  Sheet 1 of 2  4,036,722
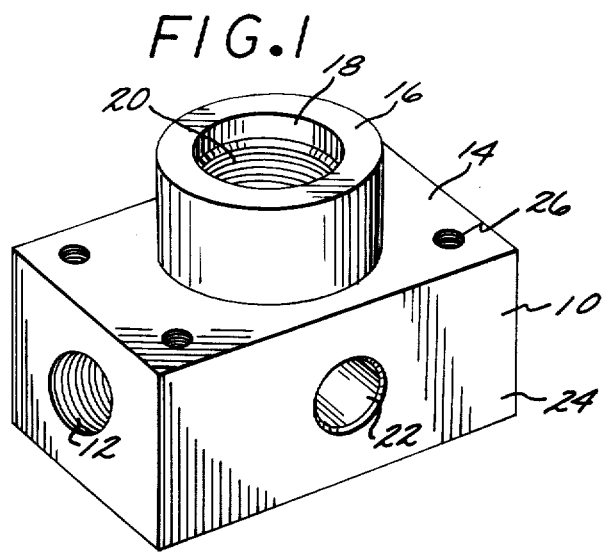
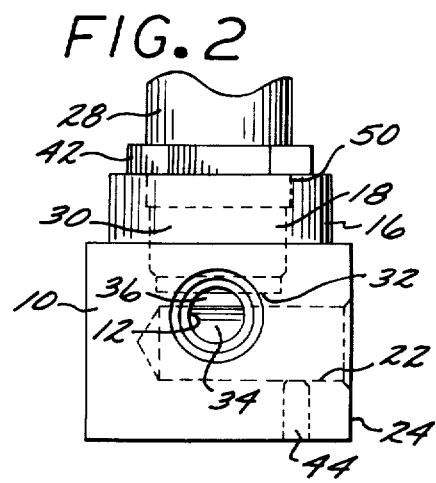
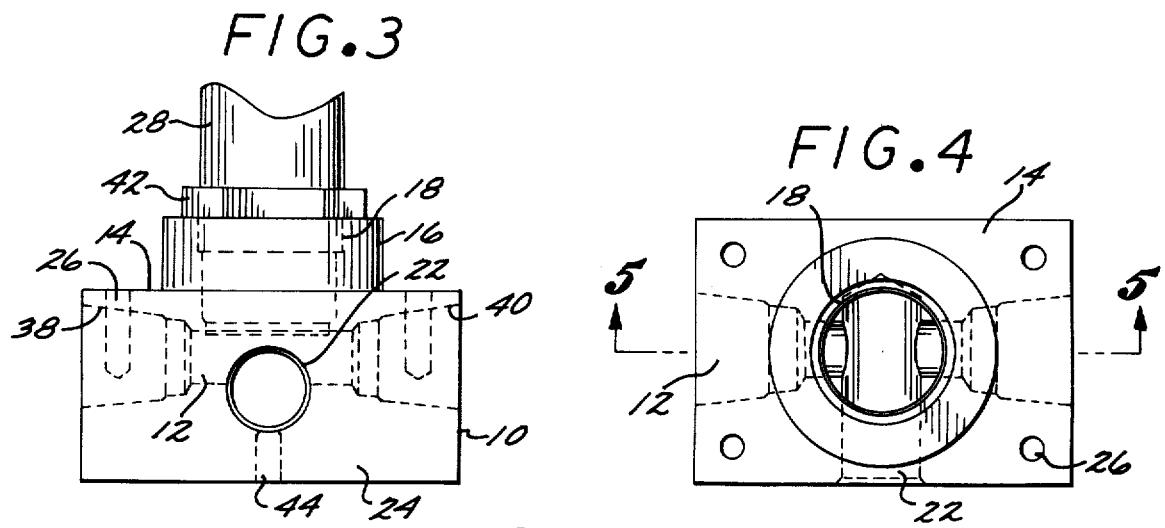
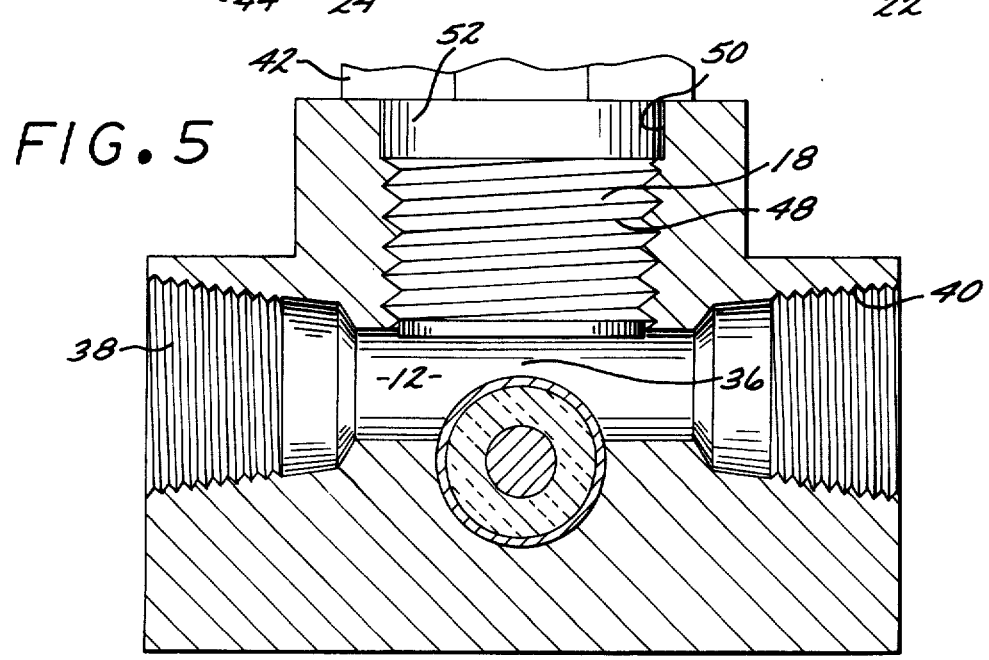

FLOW THROUGH CELL ASSEMBLY

BACKGROUND OF THE INVENTION

1. Field of the Invention

This invention relates to a cell assembly and, in particular, to a cell assembly for a sensing element sensitive to the dissolved gas content of a flowing liquid stream.

2. Brief Statement of the Prior Art

There is disclosed, in U.S. Pat. No. 3,813,325, a continuous respirometer which has dissolved oxygen cells positioned at the inlet and outlet of a tubular flow passageway for determining the dissolved oxygen contents of a liquid stream entering and exiting the respirometer. The dissolved oxygen analyses are performed on a continuously flowing liquid stream with the tips of the cathodes projecting downwardly through bores in the top walls of tubular housings. It is disclosed that the probes fare in with the surfaces of the interior walls to avoid projections on which residue may build up.

Use of the forementioned respirometer has revealed that when the probes project into the stream even by a slight distance, air pockets developed on the upstream side of the projections and these air pockets are not exhausted during the purging of the apparatus, contributing to erroneous analyses for dissolved oxygen contents.

Although not illustrated in the aforementioned patent, commercial embodiments of the patented device have employed a temperature compensation circuit having a thermistor imposed in the path of flow through the electrode housing to compensate for changes in permeability with temperature of the plastic membranes which overlie the cathode surfaces and directly affect the readings of the oxygen cells. These thermistors were placed generally transverse in the housing, beneath the dissolved oxygen electrodes to be in contact with the fluid under investigation without imposing any significant pressure drop to fluid flow through the housing.

SUMMARY OF THE INVENTION

This invention comprises a cell assembly and, in particular, an assembly including a housing for the support of an electrode for sensing the content of dissolved gases such as oxygen in a liquid stream and a temperature probe for determining the temperature of the liquid stream. The probes are mounted in a housing having a through passageway, coextensive with its major axis for passage of the fluid under investigation. The housing has a first bore transverse to the through passageway and extending through its top wall to receive the cathode case of the dissolved oxygen cell and to position the cathode surface substantially coplanar with the top wall of the through passageway.

The housing has a second bore through one of its remaining walls, generally transverse to the fluid passageway and intersecting the fluid passageway substantially subjacent the intersection therewith by the first bore. Received within the second bore is a second probe member which is in substantial flow obstruction in said through passageway to define a narrow flow orifice beneath the probe received in the first bore.

In the preferred embodiment, the cathode case of a dissolved oxygen cell is placed in the first bore and a thermistor or other temperature responsive means is placed in the second bore to provide a cell assembly that will accurately indicate dissolved oxygen contents of liquids passing through the through passageway of the housing.

BRIEF DESCRIPTION OF THE DRAWINGS

Referring now to the drawings, the invention is illustrated by the following figures:

FIG. 1 is a perspective view of the cell assembly housing;

FIGS. 2 and 3 are end and side elevation views of the cell assembly;

FIG. 5 is a sectional elevation view along line 5—5 of FIG. 2; and

DESCRIPTION OF THE PREFERRED EMBODIMENTS

Figure 6:
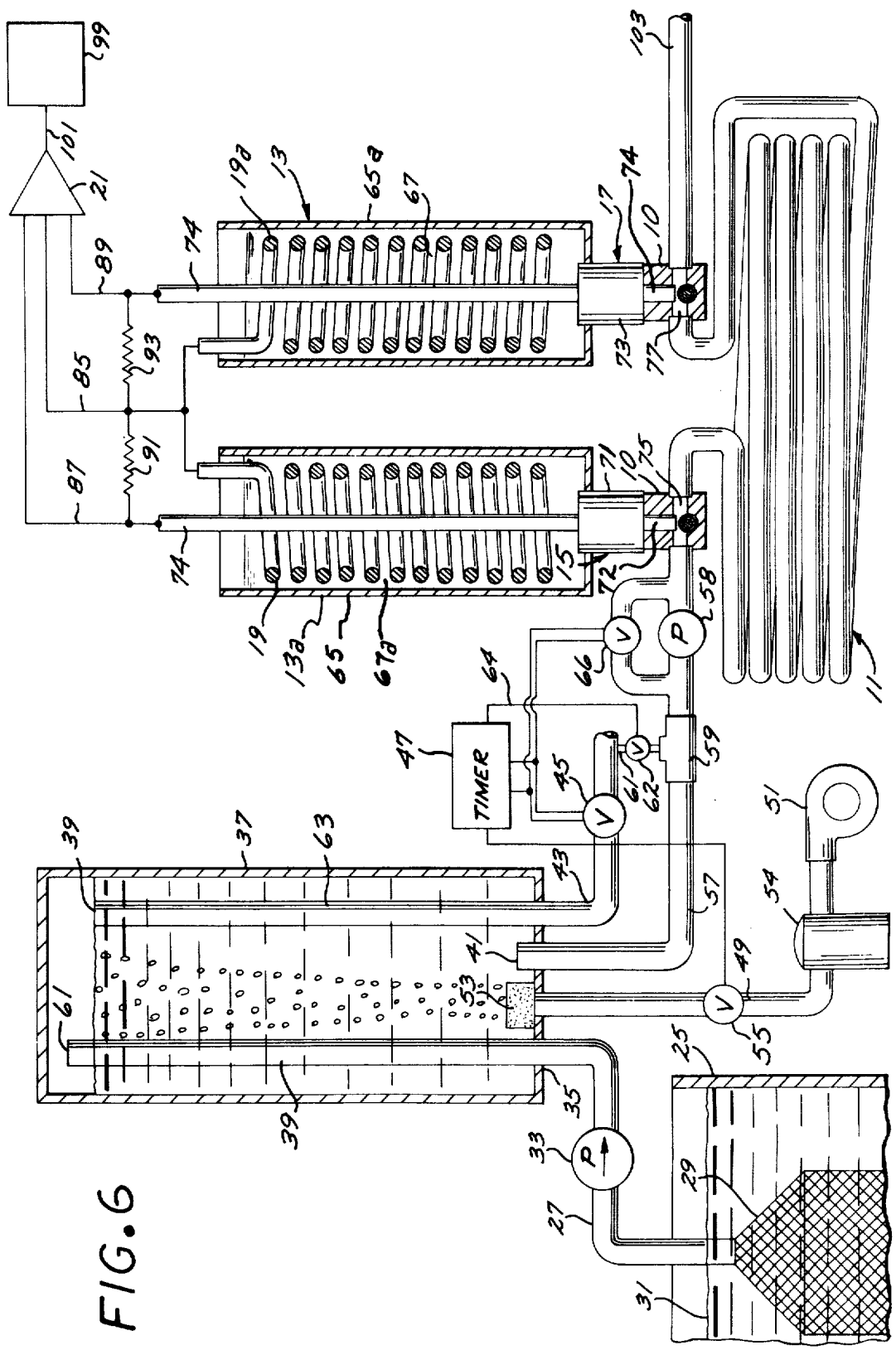
FIG. 6 illustrates a typical installation of the cell assembly of the invention.

Referring now to FIG. 1, there is illustrated a housing 10 for the cell assembly of the invention. This housing is illustrated as a member of substantially rectangular construction; other configuration can, of course, be employed. The housing 10 has a through passageway 12 which is coextensive with an axis of the housing 10; preferably coextensive with the major axis of this housing. The top surface of housing 10 bears a boss 16 which is positioned along its length and this boss is bored at 18 and bears internal threads 20 and is counterbored at 50 to provide an annular seat for an O-ring seal. Bore 18 extends into open communication with the through passageway 12 in a manner described hereinafter.

Housing 10 also bears a second bore 22 that is transverse to the through passageway 12 and extends from side 24 thereof into intersection and open communication with fluid passageway 12. Various means are also provided for securing the housing 10 in an assembly such as the internally threaded bores 26 on the upper surface 14 of the housing for receiving conventional screw fasteners and the like.

Referring now to FIGS. 2 and 3, the cell utilizing the housing 10 will be described. As illustrated in FIGS. 2 and 3, the housing 10 receives within the bore 18 of boss 16 the end of a cathode case 28 which bears a threaded neck 30 that is secured in removable engagement by internal threads 20. The bottom surface 32 of case 28 extends into the fluid passageway 12 and is generally coplanar with the top surface of through passageway 12. This substantially coplanar relationship of the top surface of passageway 12 and the under surface 32 of the cathode is important in operation of the assembly in a dissolved oxygen meter since transverse obstructions along the top surface of the fluid passageway are to be avoided or minimized in dimensions to avoid forming gas pockets in the liquid stream passing through the through passageway 12.

Bore 22 receives a generally cylindrical probe member 34 which extends transversely across the flow passageway 12. The bore 22 is positioned relative to through passageway 12 to intersect a substantial portion of the cross section of this through passageway such that probe body 34, when received in bore 22 will substantially obstruct fluid flow through through passageway 12.

Bore 22 is aligned beneath the intersection of bore 18 with through passageway 12 so that the probe body 34, when received in bore 22, will define a flow orifice 36 of minor dimensions directly beneath the undersurface 32 of probe member 28. As illustrated in FIG. 3, this can be achieved by locating the axis of bore 22 and bore 18 on a common plane, perpendicular to the axis of through passageway 12.

Referring now to FIG. 3, through passageway 12 is illustrated with counterbores 38 and 40 extending inwardly from opposite ends of the body. These counterbores are formed with conventional, internal pipe threads for receiving the threaded ends of conventional conduits. The probe body 34 can be fixedly secured within its receiving bore 22 by a set screw that is received within threaded bore 44 that projects from the bottom surface of housing 10 and intersects bore 22 as illustrated.

The top surface 14 of the cell assembly is illustrated in FIG. 4 with the preferred and generally symmetrical arrangement of the through passageway 12, top wall bore 18, side wall bore 22 and the threaded bores 26.

The sectional elevation view of FIG. 5 illustrates the conventional internal pipe threads 38 and 40 in the counterbores of through passageway 12 and the conventional internal machine screw threads 48 of bore 18. The bore 18 is also counterbored as shown at 50 to provide an annular seat for receiving the shank 52 of case 28 which bears an O-ring seal, not shown, to seal the internal chambers of housing 10 against the surrounding fluids.

The cell assembly of the invention is employed in the continuous respirometer apparatus shown in FIG. 6 which is similar to that shown in the aforementioned U.S. Pat. No. 3,813,325. As illustrated, the respirometer apparatus includes an elongated coiled residence tube 11 and oxygen sensors 13 and 13a including respective oxygen-responsive cathodes forming respective upstream and downstream cell assemblies 15 and 17 which have separate anodes 19 and 19a to generate respective electrical signals proportional to the oxygen contents of the liquid at the cell assemblies 15 and 17 which are applied to an amplifier 21 that amplifies the difference between such signals to produce an output representative of the rate of oxygen consumption during dwell time in residence tube 11.

The improved continuous respirometer apparatus includes a supply line 27 leading from the sewage tank 25 and having a coarse screen filter 29 covering the inlet thereof for filtering sewage 31 drawn into such supply line to prevent clogging thereof. The supply line 27 includes a positive displacement pump 33 which has its outlet connected with the inlet 35 in the bottom of an aerator tank 37. The supply line 27 projects upwardly in the aerator tank 37 to form a stand pipe 39 terminating in its upper extremity in an inlet port 61. An overflow stand pipe 63 also projects upwardly in the aerator tank 37 and terminates at its upper end in an overflow port 39.

The overflow stand pipe 63 has a return conduit 43 connected with the bottom thereof. While such return conduit 43 is shown as terminating in a broken end, in practice it actually connects with the tank 25 for returning sewage thereto. The overflow conduit 43 includes a solenoid valve 45 therein which is connected with a timer 47 for selective closure for predetermined periods of time when the system is to be flushed as described hereinbelow.

An aerator pipe 49 leads from an air compressor 51 to the bottom of the aerator tank 37 and has the outlet thereof capped by means of a diffuser 53 which acts to break the bubbles emitted therefrom up into tiny segments for enhancing rapid and effective dissolving thereof into the sewage. The conduit 49 also includes an air filter 54 for filtering air supplied to the aerator tank 37.

A separator conduit 57 leads from the outlet port 41 to the inlet of a metering pump 58 and includes a T-fitting forming a bubble trap 59 having a bubble escape conduit 61 leading from the side thereof. The separator conduit 57 has a sufficiently large internal diameter to provide for a sufficiently slow flow rate to give air bubbles contained in the sewage sufficient time to raise upwardly therein to be collected in the bubble trap 59 for escape to the escape conduit 61. The escape conduit 61 leads to the return conduit 43 and includes a solenoid valve 62 which is connected with the inlet to the inlet oxygen probe 15 and has a solenoid operated bypass valve 66 connected thereacross.

The oxygen sensors 13 and 13a are in the form of housings 65 and 65a, each containing a conventional electrolytic solution 67 and 67a therein. Disposed centrally in the electrolytic solution 67 and 67a are anodes 19 and 19a which serve as electrodes for the respective inlet and outlet oxygen sensing cells 15 and 17, such cells including respective cathodes 72 and 74. Projecting downwardly from the bottom wall of the oxygen sensors 13 and 13a are a pair of sensing cases 71 and 73 which form the respective inlet and outlet of the residence tube 11 and have the respective cathodes 72 and 74 projecting downwardly therein. The tips of the cases are of the construction and shape of case 28, and the cells 15 and 17 are of the construction and shape of cell housing 10, previously described.

The sensing ends of the cells 15 and 17 are in the form of permeable Teflon membranes and the fittings 71 and 73 are formed with reduced-in-diameter flow chambers 75 and 77 to accelerate fluid flowing thereby to establish a fast flow rate to maintain such membranes clear of residue and prevent the buildup of a boundary layer thereover of oxygen dissipated sewage which may result in a false reading thereby assuring exposure of the desired oxygen-containing fluid to such membranes.

The outputs from the anodes 19 and 19a and cathode 72 and 74 are connected with the input to the amplifier by means of leads 85, 87 and 89. Connected between the anode lead 85 and cathode leads 87 and 89 are resistors 91 and 93. The output from such amplifier 21 is connected with a combination visual meter and recorder 99 by means of a lead 101.

In the preferred embodiment, the residence tube 11 is constructed from a ⅜ inch inside diameter tube which is 50 feet in length to provide the desired residence time therein for an accurate indication of the rate of consumption of dissolved oxygen during flow through such tube. While it is desirable to locate cells 15 and 17 in close proximity, as shown, to minimize temperature differences this is not essential since the cells of this invention employ a temperature sensing probe that can be in a temperature compensating circuit of the dissolved oxygen cell which compensates for the temperature affects on the permeability of the membranes which overlie the cathode surfaces.

The outlet from the residence tube 11 is connected with a slighty restricted diameter dump conduit 103 leading to a dump area to thereby provide for a slight flow resistance to assure that the residence tube 11 is maintained full.

In operation, the time 46 is energized to commence periodic opening and closing of the overflow valve 45 and air bypass valve 55 and concurrent closure and opening of the metering pump bypass valve to periodically flush the residence tube 11 with a high flow rate produced by supply pump 33.

The positive displacement supply pump 33 is selected to pump sewage into the aerator 37 at a rate greater than the normal flow rate through the residence tube 11 to thereby maintain an adequate supply in the aeration chamber 37 to assure a constant supply of sewage to the metering pump 58 to thereby maintain the fluid flow through the residence tube 11 at a constant rate during sensing of the oxygen content thereof.

The air compressor 51 continually pumps air into the bottom of the aerator tank 37 through the aeration tube 49 to assure an oxygen content in the sewage entering the residence tube 11 that will be sufficient to maintain the oxygen content at the outlet of such residence tube above approximately one part per million irrespective of the rate at which bacteria therein consume such oxygen to assure an oxygen level that is readily detectable by the outlet oxygen probe 17.

Direct communication of such air from the aeration tube 49 to the outlet port 41 is prevented since air bubbled through the air diffuser 53 rises in the tank 37 thus moving away from the outlet port 41.

Any undissolved oxygen remaining in the sewage withdrawn from the tank 37 and introduced into the separator tube 57 will rise within the bubble trap 59 to escape therefrom through the bubble conduit 61 for return to the sewage tank 25.

Sewage from the bubble trap 59 is pumped through the metering 66 at a constant rate and is introduced to the inlet oxygen sensing probe 15 and the partial pressure of any oxygen therein will cause a proportionate amount of current flow from the anode 19 through resistor 91 and back to the cathode 72, thus providing a proportionate voltage drop across such resistor 91. The sewage will then flow through the residence tube 11 to provide a dwell time therein of approximately 1 minute, and the oxygen content of the sewage passing from the outlet of such tube will be detected by the outlet probe 17 to establish a proportionate voltage drop across the resistor 93, it being noted that the proportionate voltages at the outer ends of the resistors 91 and 93 are fed to the amplifier 21 through the respective leads 87 and 89 to provide an amplified differential input to the recorder 99 to indicate the rate at which the oxygen in the sewage was consumed during the dwell time in the residence tube 11. It will be appreciated that the relatively small cross sectional flow area of the residence tube 11 assures that there will be no stagnant sewage therein so the entire body of sewage flowing therethrough flows at a continuous rate to provide an accurate indication of the actual rate of oxygen consumption in such sewage. The sewage from the outlet of the residence tube 11 will flow through the dump tube 103.

At preset intervals the control panel 46 closes the aeration overflow valve 45, bubble return valve 61 an air bypass valve 55 opening the metering pump bypass valve 66 to provide a high flow rate through the residence tube for cleaning thereof. The high sewage flow rate in the metering tube 57 and residence tube 11 provides a good scrubbing action to assure cleaning of the entire system and, particularly, the Teflon membranes covering the ends of the probe cathodes 72 and 74 to provide for continued reliable operation of the system. With the bubble escape valve 62 closed, escape of air directly into the overflow tube 43 is avoided to maintain the high flow rate through the residence tube 11 during the flush period. Once the flush period is completed the timer 46 de-energizes the overflow valve 45, air bypass valve 55 and bubble escape valve 62 to re-commence steady rate of sewage flow through the residence tube 11 to continue sensing the rate at which oxygen dissolved therein is consumed.

The invention is of particular value as applied to the aforementioned continuous respirometer since the positioning of the thermistor in the flow path through each of the cell assemblies greatly reduces the flow area and increases the flow rate therethrough. Accordingly, the total flow rate through the respirometer can be quite low, providing a greatly increased residence time in the respirometer without requiring an increase in the volume of residence tube 11 over that shown in the prior U.S. Pat. No. 3,813,325.

The invention has been described with reference to the presently preferred and illustrated mode of practice. It is not intended that the invention be unduly limited by this illustration and description. Instead, it is intended that the invention be defined by the means, and their obvious equivalents, set forth in the following claims.

What is claimed is:

1. In a continuous flow respirometer having an elongated residence tube, a metering pump to force a liquid therethrough at a constant flow rate, and dissolved oxygen cells to sense the oxygen content of the liquid entering and exiting said residence tube, the improvement comprising a cell assembly for a plurality of instrument probes, one each at the inlet and outlet of said residence tube, each assembly comprising:
   a housing having a through passageway in open communication with said residence tube for transit of said stream of liquid;
   a first transverse bore extending from the top surface of said housing and intersecting said through passageway;
   a second transverse bore extending laterally from one side of said housing, intersecting said housing, intersecting said through passageway and perpendicular thereto;
   a first instrument probe meter carrying the cathode of one of said dissolved oxygen cells and mounted in said first transverse bore and terminating generally coplanar with the top surface of said through passageway; and
   a second instrument probe meter carried in said second transverse bore and extending transversely across said through passageway immediately beneath, but out of contact with, the lower end of said first instrument probe to block a substantial cross section of said through passageway and be in substantial flow obstruction to said through passageway and to define a narrow flow constriction there in immediately beneath said first probe meter.

2. The respirometer of claim 1 wherein said flow construction has a width from 0.05 to about 0.2 inch.

3. The respirometer of claim 1 wherein each of said second probe members is a temperature responsive element.

4. The respirometer of claim 3 wherein said temperature responsive elements are thermistors.

* * * * *